(12) United States Patent
Holmberg

(10) Patent No.: US 11,701,519 B2
(45) Date of Patent: Jul. 18, 2023

(54) FERRULE WITH STRAIN RELIEF SPACER FOR IMPLANTABLE MEDICAL DEVICE

(71) Applicant: Heraeus Medical Components LLC, St. Paul, MN (US)

(72) Inventor: Harold Holmberg, St. Paul, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 273 days.

(21) Appl. No.: 17/181,304

(22) Filed: Feb. 22, 2021

(65) Prior Publication Data

US 2021/0260385 A1 Aug. 26, 2021

Related U.S. Application Data

(60) Provisional application No. 62/979,565, filed on Feb. 21, 2020.

(51) Int. Cl.
*A61N 1/375* (2006.01)
*H02G 15/007* (2006.01)

(52) U.S. Cl.
CPC ......... *A61N 1/3754* (2013.01); *H02G 15/007* (2013.01)

(58) Field of Classification Search
None
See application file for complete search history.

(56) References Cited

U.S. PATENT DOCUMENTS

| 3,979,187 A | 9/1976 | Scherer |
| 4,152,540 A | 5/1979 | Duncan et al. |
| 4,217,137 A | 8/1980 | Kraska et al. |

(Continued)

FOREIGN PATENT DOCUMENTS

| CN | 102614588 | 8/2012 |
| CN | 102872529 | 1/2013 |

(Continued)

OTHER PUBLICATIONS

Hussain, et al., "Electrical conductivity of an insulator matrix (alumina) and conductor particle (molybdenum) composites". Journal of the European Ceramic Society, vol. 23, Issue 2, Feb. 2003, pp. 315-321.

(Continued)

*Primary Examiner* — Krystal Robinson
(74) *Attorney, Agent, or Firm* — Dicke, Billig & Czaja, PLLC

(57) ABSTRACT

On example provides a ferrule for an implantable medical device including a first frame body having a first perimeter surface to make a brazed connection to a first medical device component, and a second frame body having a first perimeter surface to make a welded connection to a second medical device component. A spacer flange connects a second perimeter surface of the first frame body to a second perimeter surface of the second frame body, a thickness between a top surface and bottom of the spacer flange being less than a thickness between a top surface and a bottom surface of the first frame body such that the spacer flange is to deflect relative to the first frame body in response to forces being applied to the second frame body so as to reduce transmission of weld strain from the second frame body to the first frame body.

14 Claims, 11 Drawing Sheets

(56) References Cited

U.S. PATENT DOCUMENTS

| | | |
|---|---|---|
| 4,315,054 A | 2/1982 | Sack et al. |
| 4,352,951 A | 10/1982 | Kyle |
| 4,354,964 A | 10/1982 | Hing et al. |
| 4,362,792 A | 12/1982 | Bowsky et al. |
| 4,456,786 A | 6/1984 | Kyle |
| 4,488,673 A | 12/1984 | Hopper, Jr. |
| 4,602,956 A | 7/1986 | Partlow et al. |
| 4,678,868 A | 7/1987 | Kraska et al. |
| 4,737,601 A | 4/1988 | Gartzke |
| 4,774,953 A | 10/1988 | Foote |
| 4,782,209 A | 11/1988 | Caers et al. |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,306,891 A | 4/1994 | Fleming et al. |
| 5,333,095 A | 7/1994 | Stevenson et al. |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,654,106 A | 8/1997 | Purnell et al. |
| 5,683,435 A | 11/1997 | Truex et al. |
| 5,693,580 A | 12/1997 | Brow et al. |
| 5,738,270 A | 4/1998 | Malmgren |
| 5,750,926 A | 5/1998 | Schulman et al. |
| 5,769,874 A | 6/1998 | Dahlberg |
| 5,782,891 A | 7/1998 | Hassler et al. |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,867,361 A * | 2/1999 | Wolf .................. A61N 1/3754 333/182 |
| 5,870,272 A | 2/1999 | Seifried et al. |
| 5,902,326 A * | 5/1999 | Lessar .................. A61B 5/031 607/36 |
| 5,905,627 A | 5/1999 | Brendel et al. |
| 6,093,476 A | 7/2000 | Horiuchi et al. |
| 6,232,004 B1 | 5/2001 | Lasater |
| 6,275,369 B1 | 8/2001 | Stevenson et al. |
| 6,284,080 B1 | 9/2001 | Haq et al. |
| 6,414,835 B1 | 7/2002 | Wolf et al. |
| 6,490,148 B1 | 12/2002 | Allen et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,765,779 B2 | 7/2004 | Stevenson et al. |
| 6,768,629 B1 | 7/2004 | Allen et al. |
| 6,985,347 B2 | 1/2006 | Stevenson et al. |
| 6,999,818 B2 | 2/2006 | Stevenson et al. |
| 7,035,076 B1 | 4/2006 | Stevenson |
| 7,035,077 B2 | 4/2006 | Brendel |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 | 12/2009 | Coffed et al. |
| 7,668,597 B2 | 2/2010 | Engmark et al. |
| 7,706,124 B2 | 4/2010 | Zhao et al. |
| 7,720,538 B2 | 5/2010 | Janzig et al. |
| 7,725,190 B2 * | 5/2010 | Iyer .................. A61N 1/3754 607/36 |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B2 | 3/2012 | Faraji et al. |
| 8,155,743 B2 | 4/2012 | Rundle et al. |
| 8,163,397 B2 | 4/2012 | Ok et al. |
| 8,179,658 B2 | 5/2012 | Brendel et al. |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,373,965 B2 | 2/2013 | Iyer |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,604,341 B2 | 12/2013 | Barry et al. |
| 8,653,384 B2 * | 2/2014 | Tang .................. H01R 43/00 607/116 |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 9,431,801 B2 | 8/2016 | Markham et al. |
| 9,478,959 B2 | 10/2016 | Markham et al. |
| 9,653,893 B2 | 5/2017 | Markham et al. |
| 10,418,798 B2 | 9/2019 | Markham et al. |
| 10,770,879 B2 | 9/2020 | Markham et al. |
| 2001/0013756 A1 | 8/2001 | Mori et al. |
| 2001/0018012 A1 | 8/2001 | Harmand et al. |
| 2001/0034966 A1 | 11/2001 | Golubkov et al. |
| 2001/0041227 A1 | 11/2001 | Hislop |
| 2001/0050837 A1 | 12/2001 | Stevenson et al. |
| 2002/0139556 A1 | 10/2002 | Ok et al. |
| 2002/0166739 A1 | 11/2002 | Naerheim |
| 2003/0109903 A1 | 6/2003 | Berrang et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0150020 A1 | 6/2007 | Hokanson et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |
| 2009/0192578 A1 | 7/2009 | Biggs |
| 2009/0281586 A1 | 11/2009 | Lim |
| 2010/0023086 A1 | 1/2010 | Lim |
| 2010/0109966 A1 | 5/2010 | Mateychuk et al. |
| 2010/0121438 A1 | 5/2010 | Jarvik |

(56) References Cited

U.S. PATENT DOCUMENTS

| | | |
|---|---|---|
| 2010/0202096 A1 | 8/2010 | Iyer |
| 2010/0241206 A1 | 9/2010 | Truex et al. |
| 2010/0258342 A1 | 10/2010 | Parker |
| 2010/0258540 A1 | 10/2010 | Tamura et al. |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0108320 A1 | 5/2011 | Lakner |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2012/0209100 A1 | 8/2012 | De Beeck et al. |
| 2012/0309237 A1 | 12/2012 | Marzano |
| 2013/0035733 A1 | 2/2013 | Breyen et al. |
| 2013/0060312 A1 | 3/2013 | Iyer et al. |
| 2013/0184797 A1 | 7/2013 | Tang et al. |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |
| 2014/0151114 A1* | 6/2014 | Morioka ............... H02G 3/22 174/650 |
| 2014/0262493 A1 | 9/2014 | Markham et al. |
| 2014/0262494 A1 | 9/2014 | Reisinger et al. |
| 2014/0345934 A1 | 11/2014 | Markham et al. |
| 2014/0368298 A1 | 12/2014 | Reisinger |
| 2015/0165220 A1 | 6/2015 | Markham |
| 2016/0126712 A1 | 5/2016 | Markham et al. |
| 2016/0271400 A1 | 9/2016 | Kronmueller et al. |
| 2016/0358699 A1 | 12/2016 | Stevenson et al. |
| 2019/0290921 A1 | 9/2019 | Stevenson |
| 2021/0265084 A1 | 8/2021 | Holmberg |

FOREIGN PATENT DOCUMENTS

| | | |
|---|---|---|
| DE | 69729719 | 7/2005 |
| DE | 102006054249 | 5/2008 |
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| JP | H1-148760 | 6/1989 |
| JP | H2-133378 | 5/1990 |
| WO | 03073450 | 9/2003 |
| WO | 2004110555 | 12/2004 |
| WO | 2008103166 | 8/2008 |
| WO | 2010091435 | 8/2010 |
| WO | 2013075797 | 5/2013 |

OTHER PUBLICATIONS

Gil et al., "Grain Growth Kinetics of Pure Titanium," Scripta Metallurgica et Materialia, vol. 33, No. 8, pp. 1361-1366 (Oct. 15, 1995).

Exner, Horst et al., "Laser Joining of Ceramics in Liquid Phase," pp. 1-8 (Nov. 8, 2011).

* cited by examiner

FERRULE WITH STRAIN RELIEF SPACER FOR IMPLANTABLE MEDICAL DEVICE

CROSS-REFERENCE TO RELATED APPLICATION

This Non-Provisional Patent Applications claims the benefit of the filing date of U.S. Provisional Patent Application Ser. No. 62/979,565, filed Feb. 21, 2020, ENTITLED "FERRULE WITH STRAIN RELIEF SPACER FOR IMPLANTABLE MEDICAL DEVICE," which is incorporated herein by reference.

BACKGROUND

Implantable medical devices, such as cardiac pacemakers, cardiac defibrillators, and neurostimulators, receive and/or deliver electrical signals to/from portions of the body via sensing and/or stimulating leads. Implantable medical devices typically include a metal housing (typically titanium) having a hermetically sealed interior space which isolates the internal circuitry, connections, power sources, and other device components from body fluids. A feedthrough device (often referred to simply as a feedthrough) establishes electrical connections between the hermetically sealed interior space and the exterior bodily fluid side of the device.

Feedthroughs typically include an insulator (e.g., a ceramic material) and electrical conductors or feedthrough pins which extend through the insulator to provide electrical pathways between the exterior and the hermetically sealed interior. A frame-like metal ferrule is disposed about a perimeter surface of the insulator, with the ferrule and insulator being joined to one another, such as by a brazing or soldering process. The ferrule, in-turn, is arranged to fit within a corresponding opening in the metal housing, and is mechanically and hermetically attached to the housing, typically via welding (e.g., laser welding), with the insulator electrically insulating the feedthrough pins from one another and from the metal ferrule and housing.

However, mechanical strains resulting from the welding of the ferrule to the housing can potentially damage the insulator and the interface between the insulator and the ferrule, and thereby compromise the hermetic seal between the feedthrough and the housing. For these and other reasons there is a need for the example ferrules described by the disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description, therefore, is not to be taken in a limiting sense, and the scope of the invention is defined by the appended claims.

It is to be understood that the features of the various exemplary embodiments described herein may be combined with each other, unless specifically noted otherwise.

Figure 1:
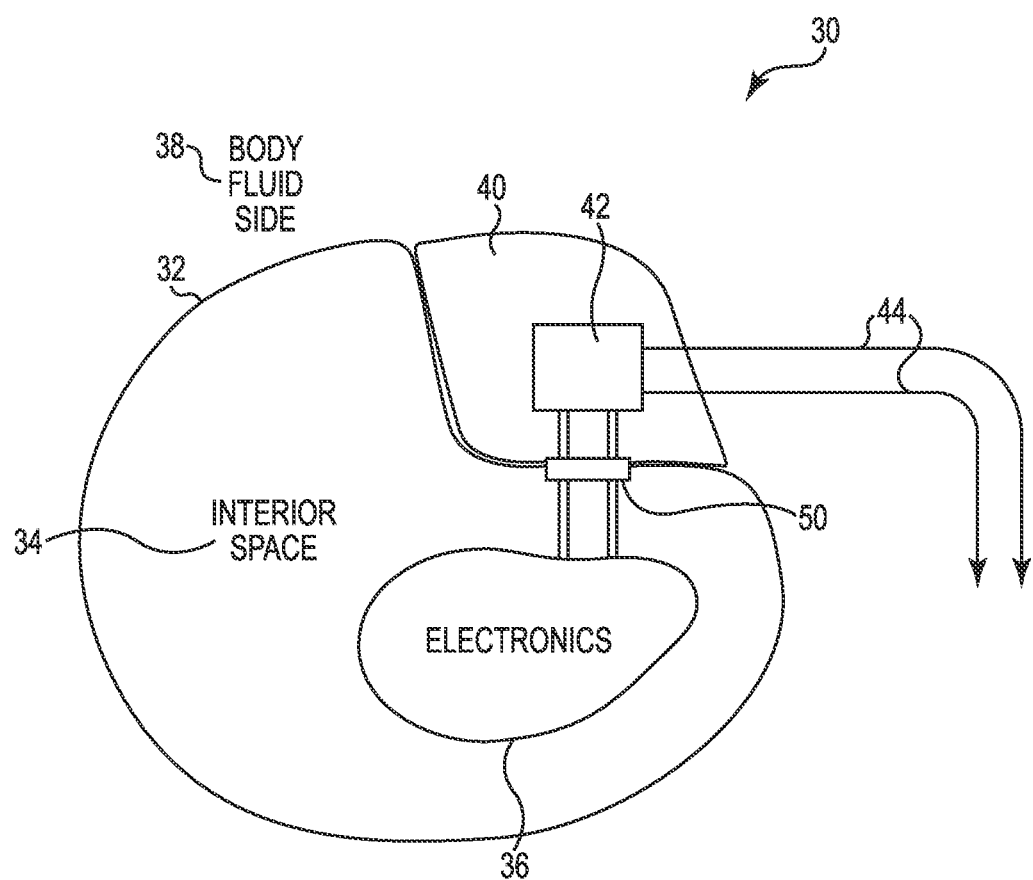
FIG. 1 is a block and schematic diagram generally illustrating an example of an implantable medical device, according to one example.

FIG. 1 is a block and schematic diagram generally illustrating an example of an implantable medical device 30 (e.g., a cardiac pacemaker) employing a feedthrough device including a ferrule in accordance with the disclosure. Implantable medical device 30 includes a hermetically sealed metal case or housing 32, typically formed of titanium, which defines a hermetically sealed interior space 34 in which device electronics 36 are disposed and protected from fluids of the body fluid side 38 external to housing 32. A header 40 attaches to housing 32 and includes a connector block 42 which typically includes one or more sockets for connecting to one or more sensing and/or stimulating leads 44 that extend between implantable medical device 30 and desired regions of the body (e.g., the human heart and brain). A feedthrough device 50 establishes electrical pathways or connections through housing 32 that maintain the integrity of hermetically sealed interior space 34 and provide electrical connection of leads 44 to internal device electronics 36.

Figure 2A:
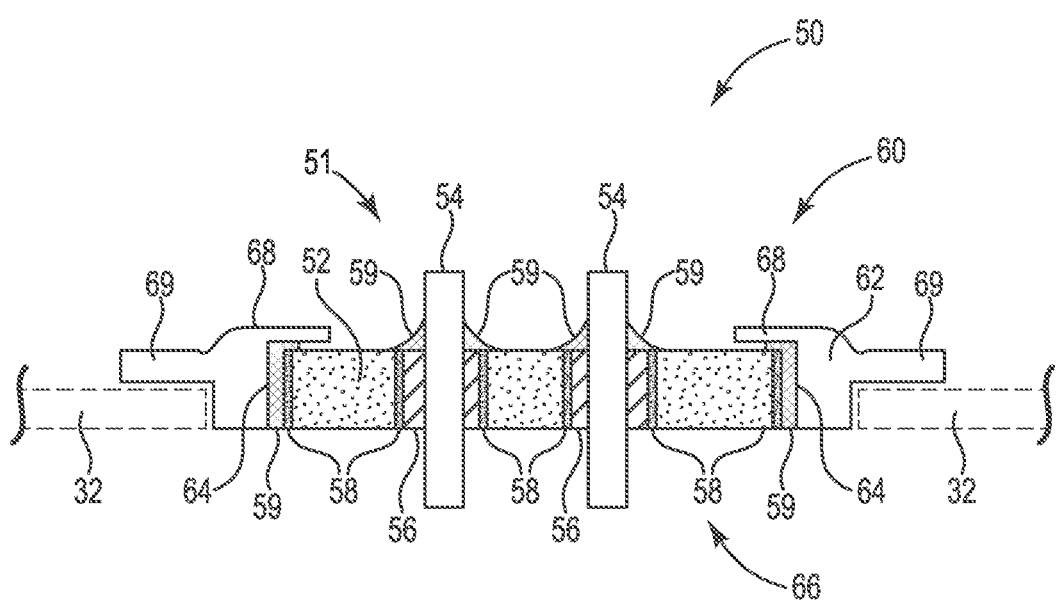
FIG. 2A is a cross-sectional view generally illustrating an example of a known feedthrough device for an implantable medical device.

FIG. 2A is a cross-sectional view generally illustrating an example of a feedthrough device 50, such as for use with medical device 30 of FIG. 1, including an insulator assembly 51 having an insulator body 52 through which pass a number of feedthrough pins or conducting elements 54, and an example of a known ferrule 60 for connecting to insulator body 52 and for connecting feedthrough device 50 to housing 32 of medical device 30.

According to one example, as illustrated, ferrule 60 includes a metal frame body 62 to which insulator 52 is attached, and which is to attach to metal housing 32 (e.g., see FIGS. 2B and 2C below). Although not explicitly illustrated in the cross-sectional view of FIG. 2A, frame body 62 is a frame-like or ring-like body having an interior perimeter surface 64 which defines an opening 66 to receive insulator body 52 and to which insulator body 52 is attached. Frame-like metal body 62 may be of any suitable geometric shape (e.g., circular, oval, rectangular, etc.). In examples, such as illustrated by FIG. 2A, ferrule 60 may include one or more flanges extending from frame body 62, such as insulator flange 68 for assisting in connection to insulator body 52, and housing flange 69 for assisting in connection to housing 32 of medical device 30. Ferrule 56 comprises a biocompatible material (e.g., titanium) which is to be mechanically and hermetically attached to housing 32, such as by laser welding, or similar techniques (see FIGS. 2B and 2C).

In one example, insulator body 52 includes a number of openings or vias 56 through which conducting elements 54 pass, where conducting elements 54 are formed of an electrically conductive material to provide electrically conductive pathways from the external body fluid side 38 of housing 32 to hermetically sealed interior space 34. Insulator body 52 is formed of a non-electrically conductive material, such as a ceramic material (e.g., aluminum oxide ($Al_2O_3$)), for example, and electrically isolates conducting elements 54 from one another and from ferrule 56 (and housing 32).

In one example, a perimeter surface of insulator body 52 is metalized (through a sputter coating process, for example) to provide a thin metal coating 58 thereon. In one example, ferrule 60 is joined to insulator 52 via metal coating 58 using a braze 59, such as of gold, for example, to form a biocompatible and hermetic seal. In one example, the interior surfaces of vias 56 are similarly coated with thin metal coating 58 and a braze 59 (e.g. gold) is used to couple conducting elements 54 to insulator 52 to form a biocompatible and hermetic seal.

Figure 2B:
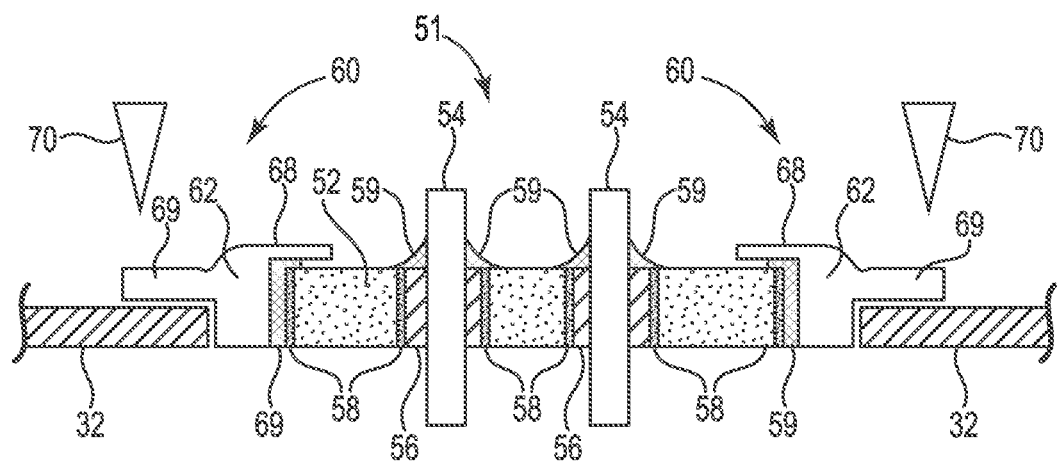
FIG. 2B is a cross-sectional view generally illustrating welding of a known feedthrough device to an implantable medical device.
Figure 2C:
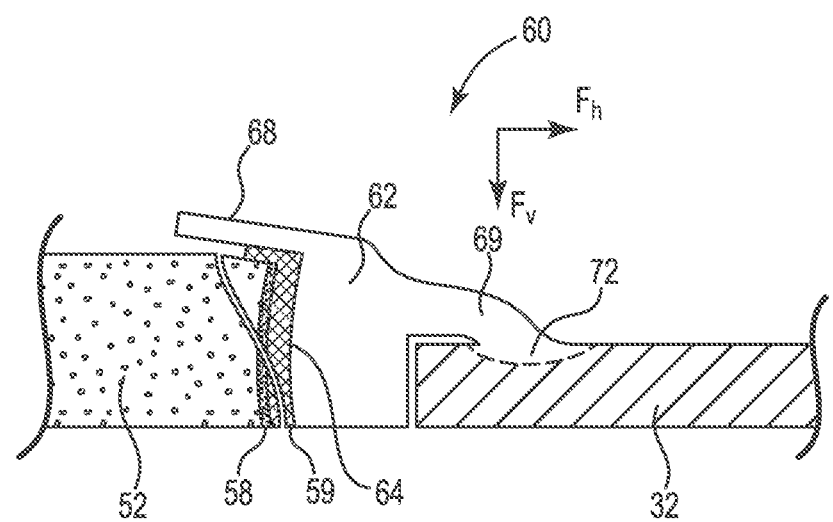
FIG. 2C is a cross-sectional view generally illustrating welding of a known feedthrough device to an implantable medical device.

With reference to FIGS. 2B and 2C, feedthrough 50 is attached to housing 32 by welding ferrule 60 to housing 32, such as by laser welding (as indicated by lasers 70), where the welded connection forms a hermetic seal between feedthrough 50 and housing 32. In one example, both ferrule 60 and housing 32 may be made of titanium. In other examples, other suitable biocompatible and weld-compatible materials may be employed.

While welding is effective at forming a hermetic seal between ferrule 60 and housing 32, the molten metal at weld joint 72 contracts as it cools. With housing 32 being generally stationary relative to ferrule 60, the contraction of weld joint 72 results in horizontal and/or vertical forces, illustrated as Fh and Fv, being applied to ferrule 60, with Fh pulling ferrule 60 toward housing 32, and Fv pulling ferrule 60 toward interior space 34 of housing 32. If contraction forces Fh and Fv are great enough, ferrule 60 may pull away and separate from insulator body 52, and may even fracture insulator body 52, thereby compromising the hermitic seal between feedthrough 50 and housing 32 and rendering medical device 30 unusable.

Figure 3:
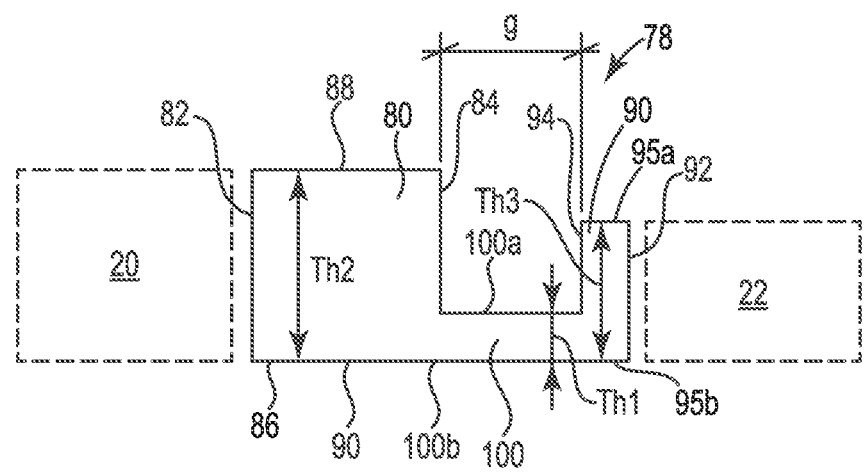
FIG. 3 is a cross-sectional view generally illustrating a portion of a ferrule for an implantable medical device, according to one example of the disclosure.

FIG. 3 is a cross-sectional view illustrating a portion of a ferrule 78 employing a strain relief spacer for use with an implantable medical device, in accordance with one example of the disclosure. In one example, ferrule 78 includes a first frame body 80 having a first perimeter surface, such as perimeter surface 82, to make a brazed connection to a first medical device component 20, and a second frame body 90 having a first perimeter surface, such as perimeter surface 92, to make a welded connection to a second medical device component 22. A spacer flange 100 extends between and connects a second perimeter surface of first frame body 80, such as perimeter surface 84, with second perimeter surface of second frame body 90, such as perimeter surface 94, so as to space and cantilever second frame body 90 from first frame body 80. In one example, first frame body 80, second frame body 90, and extension flange 90 are formed of a single, monolithic piece of material (e.g., titanium). Although not explicitly illustrated in the cross-sectional view of FIG. 3, ferrule 78 is a frame-like or ring-like body (e.g., see FIGS. 4C and 7B).

In one example, spacer flange 100 has a thickness, Th1, between a top surface 100a and a bottom surface 100b, first frame body 80 has a thickness, Th2, between a bottom surface 86 and a top surface 88, and second frame body 90 has a thickness, Th3, between a top surface 95a and a top surface 95b. In one example, thickness Th1 of spacer flange 100 is less than thickness Th2 of first frame body 80, and less than thickness Th3 of second frame body 90, such that a gap, g, is formed between first frame body 80 and second frame body 90. As will be described in greater detail below, by making spacer flange 100 thinner and, thus, less mechanically rigid than first frame body 80, spacer flange 100 deflects relative to first frame body 80 in response to forces being applied to second frame body 90 to reduce transmission of forces from second frame 90 to first frame 80, such as weld strain from the second frame body to the first frame body, for example, and thereby reduce potential strain on a braze connection, for example.

As will be described in great detail below, first medical device component 20 may be any number of components, such as a medical device housing and a feedthrough assembly, for example, and second medical device component 22 may be any number of components, such as a medical device housing or another metallic component, such as a ferrule of another component, for example.

Figure 4A:
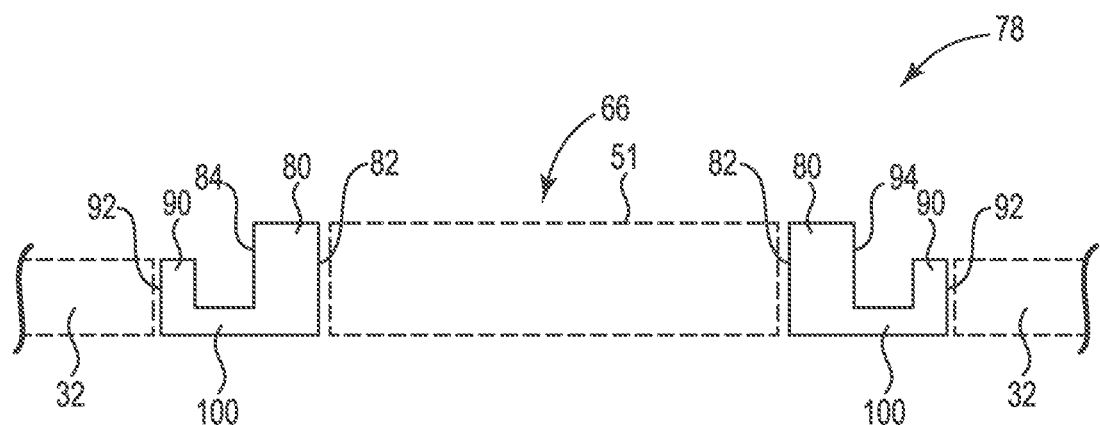
FIG. 4A is a cross-sectional view generally illustrating a ferrule, according to one example of the disclosure, for use with a feedthrough device for an implantable medical device.
Figure 4B:
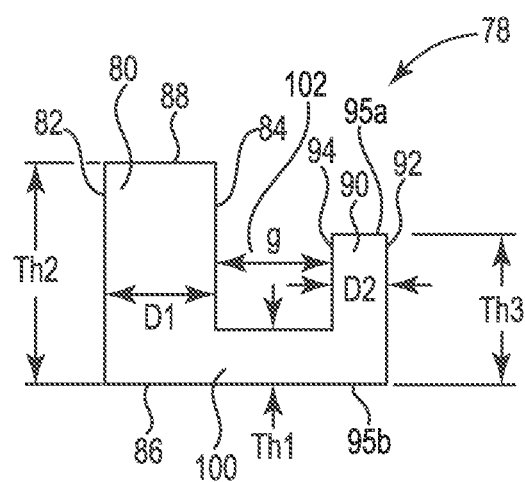
FIG. 4B is a cross-sectional view generally illustrating a portion of the ferrule of FIG. 4A, according to one example of the disclosure, for use with a feedthrough device for an implantable medical device.
Figure 4C:
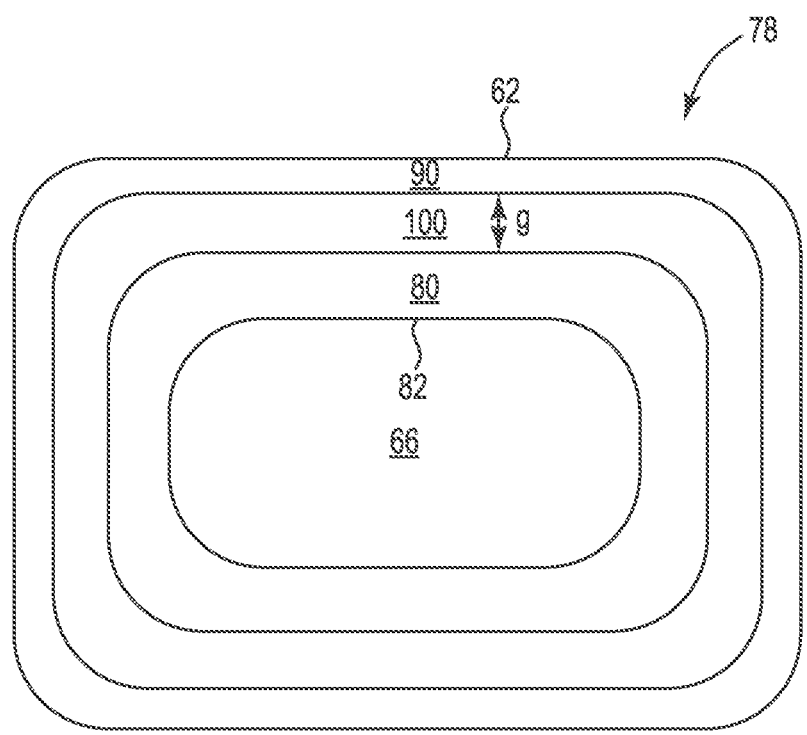
FIG. 4C is a top view generally illustrating the ferrule of FIGS. 4A and 4B, according to one example of the disclosure, for use with a feedthrough device for an implantable medical device.

FIGS. 4A-4C generally illustrate one example of a ferrule 78, in accordance with the application, which, as will be described in greater detail below, reduces or inhibits transmission of mechanical strain to insulator body 52 and to the braze joint between ferrule 78 and insulator body 52 created by the welding of ferrule 80 to housing 32.

FIG. 4A is a cross-sectional view of ferrule 78, where ferrule 78 includes a first frame body 80 having a perimeter surface 82 for attachment to insulator assembly 51, and a second frame body 90 having a perimeter surface 92 for attachment to a housing 32. In one example, as illustrated, perimeter surface 82 of first frame body 80 is continuous interior surface defining an interior opening 66 to receive insulator assembly 51, and perimeter surface 92 of second frame body 90 is a continuous exterior surface for connecting to housing 32 (e.g., via welding). A spacer flange 100 extends between and connects first frame body 80 with second frame body 90 so as to space second frame body 90 from first frame body 80. In one example, first frame body 80, second frame body 90, and extension flange 90 are of a single, monolithic piece of material (e.g., titanium).

FIG. 4B is an enlarged cross-sectional view of a portion of ferrule 78. In one example, as illustrated, spacer flange 100 extends between an exterior perimeter surface 84 of first frame body 80, which is opposite perimeter surface 82, to a perimeter surface 94 of second frame body 90, which is opposite perimeter surface 92, where perimeter surface 92 represents an exterior perimeter surface of second frame body 90 and perimeter surface 94 represents an interior perimeter surface of second frame body 90. While extension flange 100 is illustrated in FIG. 4 as extending from exterior perimeter surface 84 in a fashion flush with a bottom surface 86 of first frame body 80, in other examples, extension flange 100 may extend from exterior perimeter surface 84 at any position between bottom surface 86 and top surface 88. Additionally, in other examples, extension flange 100 may extend from a perimeter surface of first frame body 80 other than a perimeter surface which is opposite the perimeter surface 82 to which housing 32 is to be attached (e.g., see FIG. 7A).

Continuing with FIG. 4B, first frame body 80 has depth, D1, between perimeter surfaces 82 and 84, and second frame body 90 has a depth, D2, between perimeter surfaces 92 and 94. In one example, as illustrated, D2<D1. Additionally, as described above, spacer flange 100 has a thickness, Th1, between top and bottom surfaces 100a and 100b, while first and second frame bodies 80 and 90, respectively, have thicknesses Th2 and Th3. In one example, as illustrated, spacer flange 100 extends perpendicularly to perimeter surfaces 94 and 94. In one example, Th1<Th3<Th2, such that first and second frame bodies 80 and 90 and spacer flange 100 together form a channel 102 that spaces second frame body 90 from first frame body 80 body a gap distance, g, of channel 102.

As will be described in greater detail below (e.g., FIGS. 6B and 6C), by spacing second frame body 90 from first frame body 80 via spacer flange 100, and by making second frame body 90 and spacer flange 100 less mechanically rigid relative to first frame body 80 (e.g., D2<D1; Th1<Th3<Th2), ferrule 78, according to the application, reduces the transfer of mechanical strain to first frame body 80 and the braze joint with insulator body 52 caused by weld forces Fh and Fv introduced by welding of second frame body 90 to housing 32.

Figure 7A:
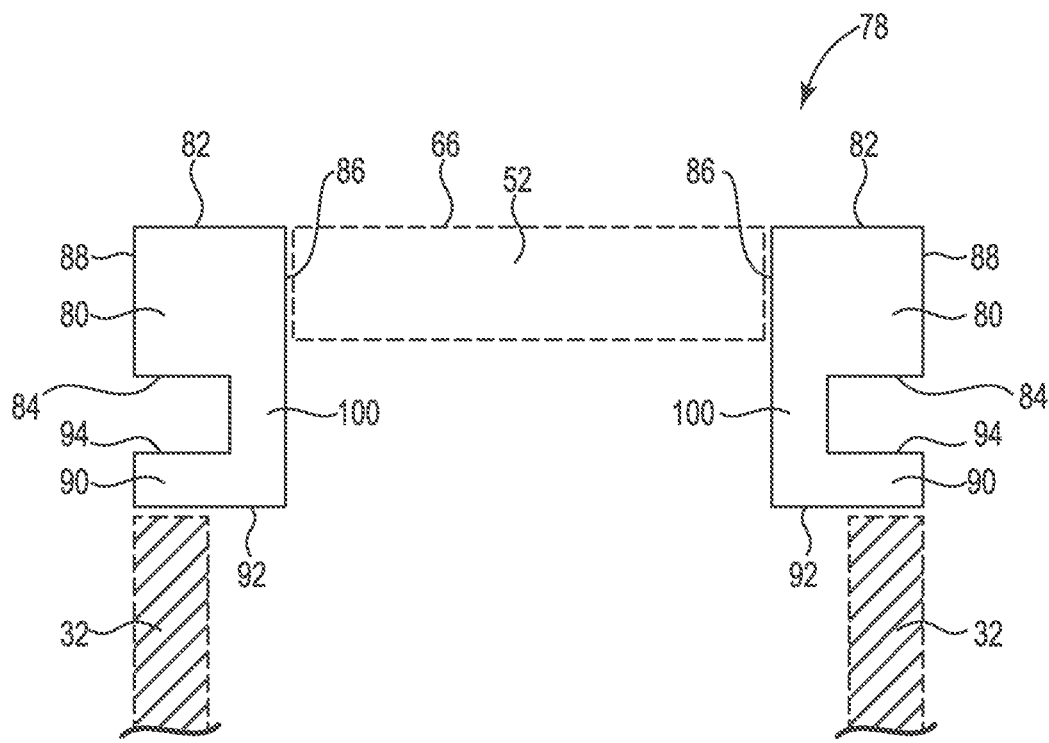
FIG. 7A is a cross-sectional view generally illustrating a ferrule, according to one example of the disclosure, for use with a feedthrough device for an implantable medical device.
Figure 7B:
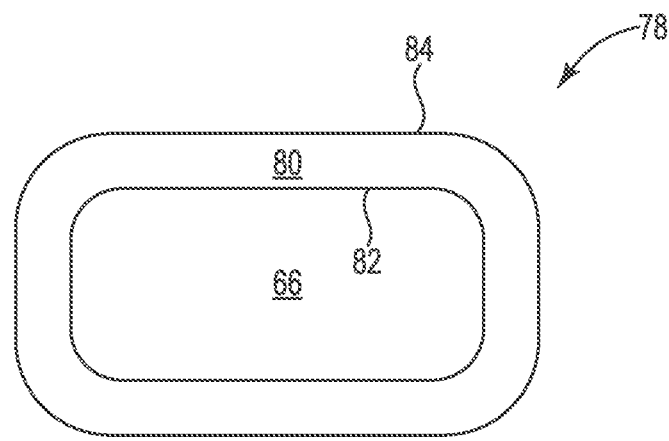
FIG. 7B is a top view generally illustrating the ferrule of FIG. 7A, according to one example of the disclosure, for use with a feedthrough device for an implantable medical device.

FIG. 4C is top view of ferrule 78 of FIGS. 4A and 4B illustrating interior opening 66 defined by interior perimeter surface 82 of first frame body 80, and second frame body 90 spaced from first frame body 80 by gap, g, by spacer flange 100. In the example implementation of FIGS. 4A-4C, first and second frame bodies 80 and 90 are concentric relative to one another, with first frame body 80 representing a first or inner ferrule for connection to insulator body 52, and second frame body 90 representing a second or outer ferrule for connection to housing 32. In other implementations, such as illustrated by FIGS. 7A and 7B below, first and second frame bodies 80 and 90 may be parallel with one another rather than concentric. Also, while illustrated as being generally rectangular in shape in FIG. 4C, first and second frame bodies 80 and 90, and s spacer flange 100 may have any suitable geometric shape (e.g., oval, circular). By employing a first ferrule (e.g., first frame body 80) for connection to the insulator body, and a second ferrule (e.g., second frame body 90) for connection to the housing, and by cantilevering the second ferrule from the first ferrule (via spacer flange 100) and making the cantilever and second ferrule less mechanically rigid than the first ferrule, ferrule 78, as disclosed herein, reduces mechanical strain on the connection between the first ferrule and the insulator body generated by welding of the second ferrule to the housing.

Figure 5:
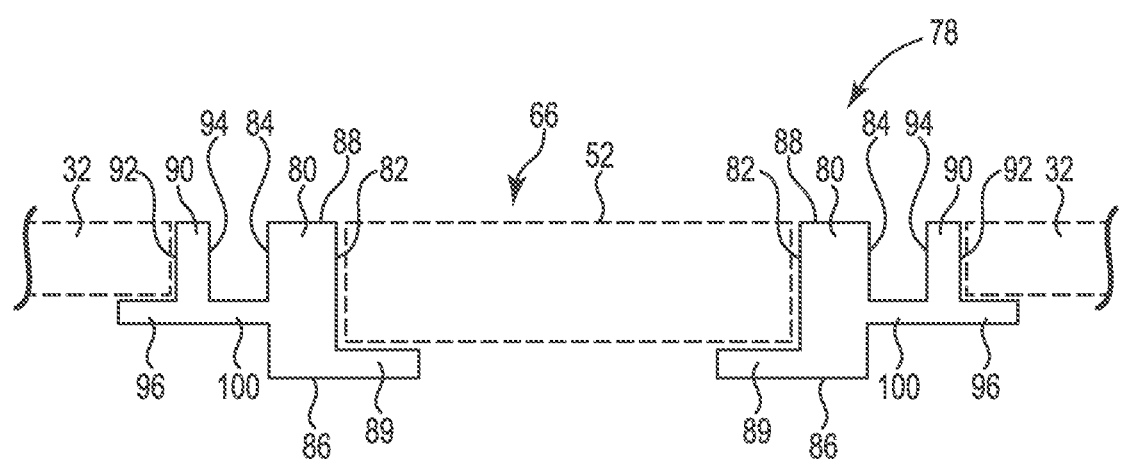
FIG. 5 is a cross-sectional view generally illustrating a ferrule, according to one example of the disclosure, for use with a feedthrough device for an implantable medical device.

FIG. 5 is a cross-sectional view illustrating another example of ferrule 78, in accordance with the disclosure. The implementation of FIG. 5 is similar to the example of FIGS. 4A-4C, except that first frame body 80 includes an insulator flange 89 extending from interior perimeter surface 82 to provide assistance in attachment of insulator body 52 to first frame body 80, and second frame body 90 includes a housing flange 96 to provide assistance in attachment of housing 32 to second frame body 90. Additionally, spacer flange 100 is not disposed flush with bottom surface 86 of first frame body 80, but is positioned along exterior perimeter surface 84 between bottom and top surfaces 86 and 88 such that housing 32 is generally flush with insulator body 52.

Figure 6A:
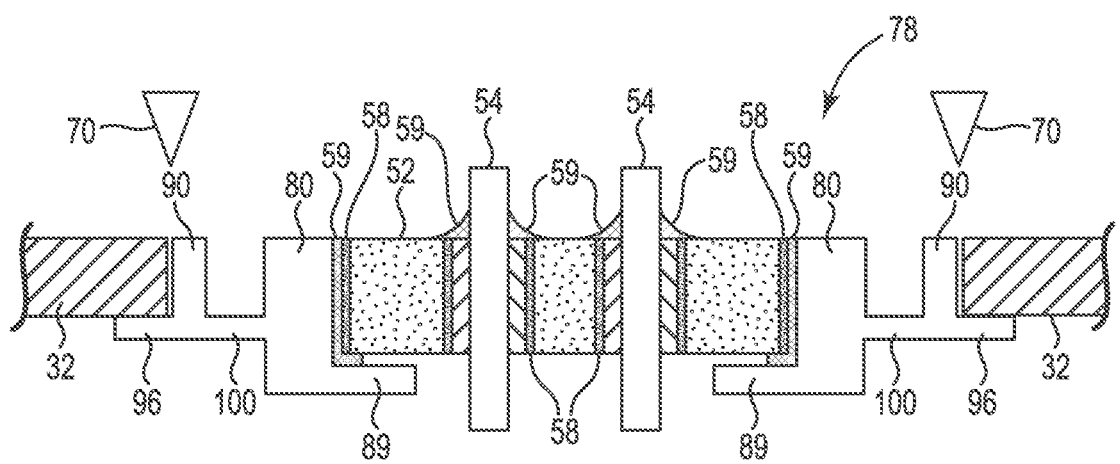
FIG. 6A is a cross-sectional view generally illustrating welding of a feedthrough device including the ferrule of FIG. 5 to a housing, according to one example of the disclosure.
Figure 6B:
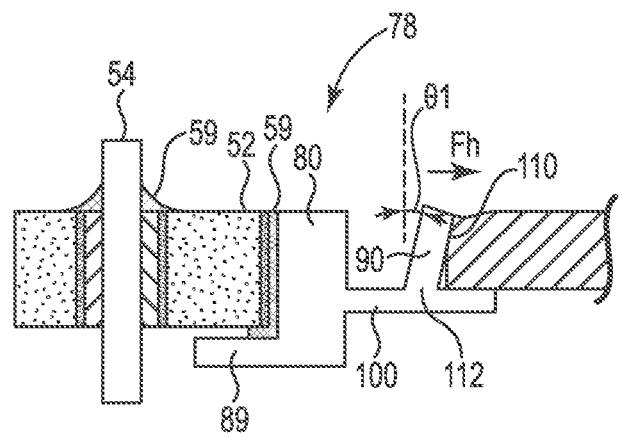
FIG. 6B is a cross-sectional view generally illustrating the welding of the ferrule of FIG. 5 to a housing, according to one example of the disclosure.
Figure 6C:
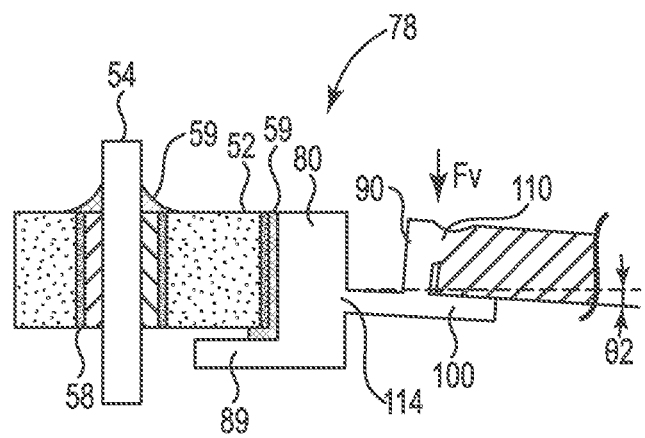
FIG. 6C is a cross-sectional view generally illustrating the welding of the ferrule of FIG. 5 to a housing, according to one example of the disclosure.

FIGS. 6A-6C are cross-sectional views generally illustrating the welding of feedthrough device 50 employing ferrule 78 of FIG. 5, in accordance with the disclosure, to housing 32, such as via laser welding (as indicated by lasers 70). FIG. 6B is an enlarged view illustrating portions of feedthrough device 50 of FIG. 6A. In one example, if horizontal weld force, Fh, generated by cooling and contraction of weld joint 110 is great enough, horizontal force Fv results in enough torque being applied to second frame body 90 to deflect frame body 90 about its base 112 where it joins extension flange 100, as indicated by deflection angle θ1. In one example, the magnitude of horizontal force, Fh, needed to generate enough torque to deflect second frame body 90 about base 112 is less than an amount of horizontal force, Fh, needed to apply enough torque to first frame body 80 (via spacer flange 100) to damage braze joint 59 between first frame body 80 and insulator body 52 and/or to fracture insulator body 52.

With reference to FIG. 6C, if vertical weld force, Fv, generated by cooling and contraction of weld joint 110 is great enough, vertical force Fv results in enough torque being applied to second frame body 90 to deflect spacer flange 100 about its base 114 where it joins first frame body 80, as indicated by deflection angle θ2. In one example, the magnitude of vertical force, Fv, needed to generate enough torque to deflect spacer flange 100 about base 114 is less than an amount of vertical force, Fv, needed to apply enough torque to first frame body 80 to damage braze joint 59 between first frame body 80 and insulator body 52 and/or to fracture insulator body 52.

By employing second frame body 90 for connecting to housing 32, and by spacing second frame body 90 from first frame body 80 and making second frame body 90 and spacer flange 100 less mechanically rigid relative to first frame body 80 and braze joint 59, ferrule 78, in accordance with the application, reduces transmission of mechanical strain to first frame body 80, braze joint 59, and insulator body 52. Instead, such mechanical strain is relieved via deflection of second frame body 90 and spacer flange 100 by horizontal and vertical weld forces Fh and Fv, with weld joint 110 continuing to provide a hermetic seal between housing 32 and second frame body 90.

Figure 6D:
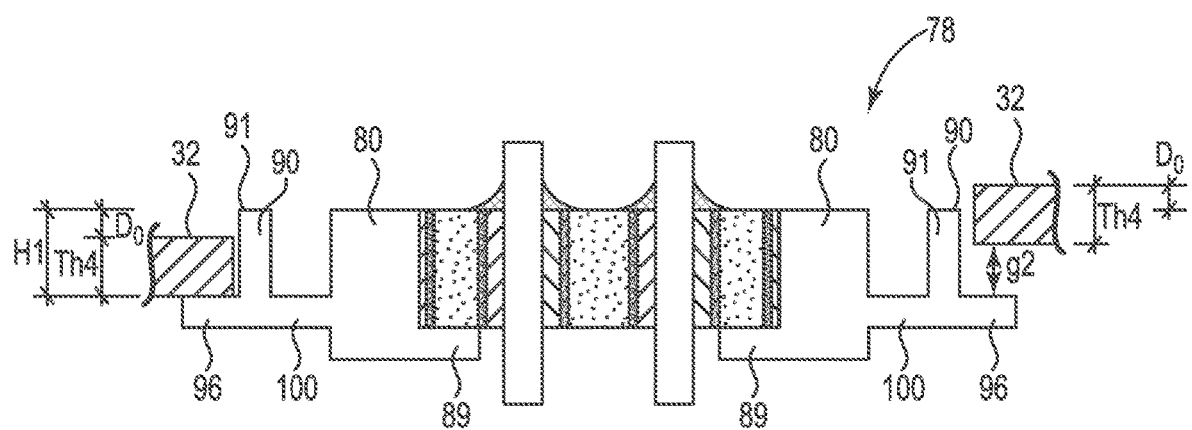
FIG. 6D is a cross-sectional view generally illustrating an example of a feedthrough device including a ferrule in accordance with the disclosure.

FIG. 6D is a cross-sectional view generally illustrating another example of ferrule 78, in accordance with the example. In the example implementation of FIG. 6D, second frame body 90 extends to a height, H1, above housing flange 96 which is greater than a thickness, Th4, of housing 32 to better enable successful welds to be made between second frame body 90 and housing 32 when housing 32 is non-planar, as illustrated by the gap, g2, between housing flange 96 and housing 32 on the right-hand side of FIG. 6D. In one example, when an offset distance, Do, between housing 32 and top surface 91 of second frame body 90 does not exceed 50% of the thickness, Th4, of housing 32, a successful weld is possible between housing 32 and second frame body 90.

FIGS. 7A and 7B respectively illustrate cross-sectional and top views generally illustrating another example of ferrule 78, in accordance with the disclosure. In the example implementation of FIGS. 7A and 7B, rather than being concentrically positioned relative to one another, such as illustrated by FIG. 5, first and second frame bodies 80 and 90 are positioned parallel with one another. Rather than extending from a perimeter surface of first frame body 80 which is opposite interior perimeter surface 82 to which insulator body 52 is to be connected, spacer flange 100 extends from bottom surface 86. Deflection of second frame body 90 and spacer flange 100 in response to weld forces resulting from welding of housing 32 to exterior perimeter surface 92 of frame body 90 is similar to that described above by FIGS. 6A-6C.

Figure 8:
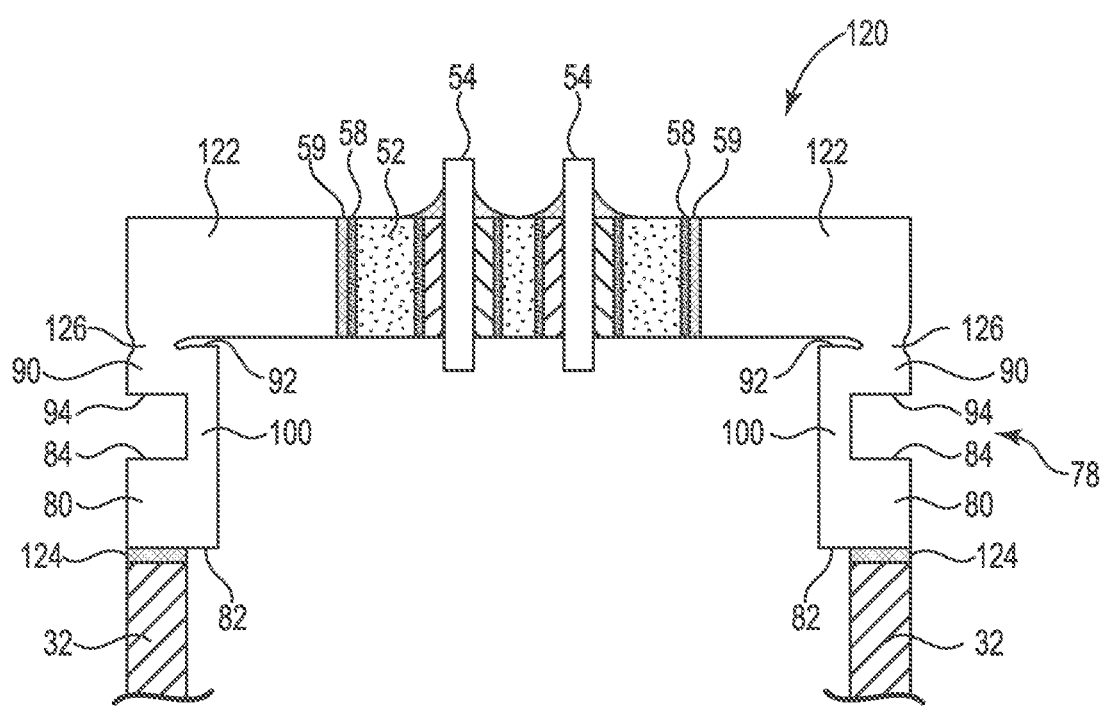
FIG. 8 is a cross-sectional view generally illustrating a ferrule for an implantable medical device, according to one example of the disclosure.

FIG. 8 illustrates another example of ferrule 78, according to the example, where ferrule 78 is employed to connect housing 32 (e.g., a ceramic housing 32) to a metal ferrule 122 of a feedthrough device 120, where metal ferrule 122 is connected to insulator assembly 51 via braze joint 59. In one example, perimeter surface 82 of first frame body 80 is first connected to housing 32 (where housing 32 comprises a ceramic material) via a braze joint 124. Subsequently, perimeter surface 92 of second frame body 90 is welded to metal ferrule 122 of feedthrough device 120, as indicated by weld joint 126, where spacer flange 100 reduces weld strain on braze joint 124 resulting from cooling of weld joint 126.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof.

What is claimed is:

1. A ferrule for an implantable medical device comprising:
   a first frame body having a first perimeter surface to make a brazed connection to a first medical device component, and an opposing second perimeter surface;
   a second frame body having a first perimeter surface to make a welded connection to a second medical device component, and an opposing second perimeter surface facing the second perimeter surface of the first frame body; and
   a spacer flange extending between and connecting the second perimeter surface of the first frame body with the second perimeter surface of the second frame body, a thickness between a top surface and bottom of the spacer flange being less than a thickness between a top surface and a bottom surface of the first frame, and a depth between the first and second perimeter surfaces of the second frame body being less than a depth between the first and second perimeter surface of the first frame body such that the spacer flange and second frame body are to deflect relative to the first frame body in response to forces being applied to the second frame body so as to reduce transmission of weld strain from the second frame body to the first frame body.

2. The ferrule of claim 1, the first medical device component comprising an insulator body of an insulator assembly, and the second medical device component comprising a medical device housing.

3. The ferrule of claim 2, the first and second surfaces of the first frame body being non-parallel to one another, and the first and second perimeter surfaces of the second frame body being opposing perimeter surfaces.

4. A ferrule for an implantable medical device comprising:
   a first frame body having a first perimeter surface to make a brazed connection to a first medical device component;
   a second frame body having a first perimeter surface to make a welded connection to a second medical device component; and
   a spacer flange extending between and connecting a second perimeter surface of the first frame body with a second perimeter surface of the second frame body, a thickness between a top surface and bottom of the spacer flange being less than a thickness between a top surface and a bottom surface of the first frame such that the spacer flange is to deflect relative to the first frame body in response to forces being applied to the second frame body so as to reduce transmission of weld strain from the second frame body to the first frame body, the first medical device component comprising an insulator body of an insulator assembly, and the second medical device component comprising a medical device housing, and the second frame body including a housing flange extending perpendicularly from the first perimeter surface, a height of the second frame body extending perpendicularly from the housing flange being greater than a thickness of the medical device housing by up to 50 percent the thickness of the medical device housing.

5. The ferrule of claim 1, the first medical device component comprising a medical device housing, and the second medical device component comprising a ferrule of a feedthrough device.

6. The ferrule of claim 5, the first and second perimeter surfaces of the first frame body being opposing perimeter surfaces, and the first and second perimeter surfaces of the second frame body being opposing perimeter surfaces.

7. A ferrule for an implantable medical device, the ferrule comprising:
- a first frame body having a first perimeter surface for making a braze connection to attach to an insulator assembly of the implantable medical device, and having a second perimeter surface opposite the first perimeter;
- a second frame body having a first perimeter surface for making a welded connection to attach to a housing of the implantable medical device, and having a second perimeter surface opposite the first perimeter surface; and
- a spacer flange that connects between the second perimeter surfaces of the first frame body and the second perimeter of the second frame body to and cantilever the second frame body from the first frame body, a depth between the first and second perimeter surfaces of the second frame body being less than a depth between the first and second perimeter surfaces of the first frame body such that the spacer flange and second frame body deflect relative to the first frame body in response to forces applied to the second frame body to limit transfer of forces from the second frame body to the first frame body.

8. The ferrule of claim 7, a thickness between a top and bottom surface of the spacer flange being less than a thickness of the first frame body in a direction parallel to the second perimeter surface.

9. The ferrule of claim 7, wherein the spacer flange extends perpendicularly between first frame body and the second frame body.

10. The ferrule of claim 7, the first perimeter surface of the first frame body being an interior perimeter surface defining an interior opening for attachment to the insulator assembly, the second perimeter surface of the first frame body being an exterior perimeter surface opposite the interior perimeter surface, the spacer flange extending from the exterior surface of the first frame body to the second perimeter surface of the second frame body, the second perimeter surface of the second frame body being an interior perimeter surface and the first perimeter surface of the second frame body being an opposing exterior perimeter surface for attachment to the housing.

11. The ferrule of claim 7, the first frame body disposed concentrically with the second frame body.

12. The ferrule of claim 7, the first frame body disposed in parallel with the second frame body.

13. A feedthrough device for an implantable medical device comprising:
- a ferrule, the ferrule comprising:
  - a first frame body having a first perimeter surface defining an interior opening, and having a second perimeter surface extending perpendicularly from the first perimeter surface;
  - a second frame body having a first perimeter surface to attach to a housing of the implantable medical device, and a having a second perimeter surface opposite to the first perimeter surface and facing the second perimeter surface of the first frame body; and
  - a spacer flange that connects between the second perimeter surface of the first and the second perimeter surface of the second frame body to cantilever the second frame body from the first frame body, the spacer flange to deflect relative to the first frame body in response to forces applied to the second frame body to reduce transfer of forces from the second frame body to the first frame body; and
- an insulator assembly disposed within the interior opening, the insulator body including:
- an insulator body hermetically coupled to the first perimeter surface of the first frame body; and
- a number of conductive elements extending through the insulator body.

14. The feedthrough device of claim 13, wherein the first and second perimeter surfaces of the second frame body are disposed perpendicularly to the first perimeter surface of the first frame body.

\* \* \* \* \*